US00PP15071P2

(12) United States Plant Patent
de Groot

(10) Patent No.: US PP15,071 P2
(45) Date of Patent: Aug. 3, 2004

(54) HYBRID TEA ROSE PLANT NAMED 'RUIY5991'

(50) Latin Name: *Rosa hybrida*
Varietal Denomination: RUIY5991

(75) Inventor: Henk C. A. de Groot, De Kwakel (NL)

(73) Assignee: De Ruiter's Nieuwe Rozen B.V., De Kwakel (NL)

( * ) Notice: Subject to any disclaimer, the term of this patent is extended or adjusted under 35 U.S.C. 154(b) by 0 days.

(21) Appl. No.: 10/437,875

(22) Filed: May 13, 2003

(51) Int. Cl.[7] ..... A01H 5/00
(52) U.S. Cl. ..... Plt./131
(58) Field of Search ..... Plt./131

*Primary Examiner*—Anne Marie Grunberg
*Assistant Examiner*—June Hwu
(74) *Attorney, Agent, or Firm*—Christie, Parker & Hale, LLP

(57) ABSTRACT

A new and distinct Hybrid Tea Rose plant having attractive red and white bicolor flowers.

1 Drawing Sheet

Classification: The present invention relates to a new Rosa hybrida L. plant.

Varietal denomination: The new plant has the varietal denomination 'RUIY5991'.

BACKGROUND OF THE INVENTION

The present invention relates to a new and distinct variety of rose plant of the Hybrid Tea rose class, which was created by crossing as seed parent an unnamed, undistributed seedling and as a pollen parent the variety known as 'RUIZON', unpatented.

SUMMARY OF THE INVENTION

Among the novel characteristics possessed by this new variety which distinguishes it from its parents and all other varieties of which I am aware are its attractive red and white bicolor flowers.

Asexual reproduction by propagation by grafting of the new variety as performed in De Kwakel, The Netherlands shows that the foregoing and other distinguishing characteristics come true to form and are established and transmitted through succeeding propagation.

COMPARISON WITH PARENTS

Among other respects, the new variety differs from its parents in flower color, inasmuch as the seed parent has flowers that are red inside and white outside; and the pollen parent has red flowers, whereas the new variety has flowers that are red inside and white outside with the red color being brighter than the seed parent.

BRIEF DESCRIPTION OF ILLUSTRATION

The accompanying illustration shows a typical specimen of the new variety depicted in color as nearly true as is reasonably possible to make the same in a color illustration of this character. In the illustration are shown: new growth 1; leaflets 2, 3 and 4; stem with thorns 5; flowers in different stages of development 6, 7, 8 and 9; and reproductive organs 10, 11 and 12.

DESCRIPTION OF THE NEW VARIETY

The following is a detailed description of the new variety with color terminology in accordance with The Royal Horticultural Society Colour Chart (R.H.S.C.C.). The terminology used in color description herein refers to plate numbers in the aforementioned color chart. Phenotypic expression may vary with light availability, environmental and cultural conditions.

The following observations are made of 9-month old plants grown in a greenhouse in De Kwakel, The Netherlands during January from a grafted cutting.

FLOWER

Blooming habit: Continuous.

*Bud.*—Size: About 6 cm long and 5 cm wide. Form: Broad ovate. Color Outside: Near 62D. Inside: Near 53A.

*Sepals.*—Margin: Foliaceous appendages usually on 2 of the 5 sepals, size about 5 to 6 cm long and about 0.5 to 0.8 cm wide. Color: Upper Surface: Near 131A. Undersurface: Near 137C.

*Peduncle.*—Length: About 15 cm. Aspect: Top about 5 cm. Is smooth; bottom hirsute. Strength: Strong. Color: Near 137C.

*Bloom.*—Size: About 14 cm. Borne: Singly. Form: Side view of upper part is convex; side of view of lower part is concave. Petalage: About 36 petals.

*Color ⅓ to ½ open*).—Outer Petals. Top Surface: Near 57A. Undersurface: Near 49D. Inner Petals Top Surface: Near 57A. Undersurface: Near 49D. Base of Petals (point of attachment): Near 4C to 4D to 49D to 57A. General tonality from a distance: Red and white bicolor.

*Color* (*fully open*).—Outer Petals. Top Surface: Near 57A. Undersurface: Near 49D. Inner Petals Top Surface: Near 57A. Undersurface: Near 49D. Base of Petals (point of attachment): Near 4C to 49D to 57A. General tonality from a distance: Red. Color Change: None. General tonality from a distance: Red.

*Petals.*—Texture: Smooth. Appearance Inside: Velvety. Outside: Velvety to satiny. Size: width about 5 cm and length about 2–3 cm. Margin: Entire.

*Form.*—Fan shape.
*Arrangement.*—Imbricated.
*Petaloids in center.*—Many, about 19, top surface near 59B, under surface near 70B, length about 15 to 25 mm, width about 5 to 20 mm, surface texture velvety.
*Persistence.*—Persistent.
*Fragrance.*—None.
*Lasting quality.*—On the plant: About 14 days. In the vase: About 9 days.

REPRODUCTIVE ORGANS

Stamens, filaments and anthers:
*Arrangement.*—Irregularly arranged around styles.
*Color.*—Stamens Filaments: Bottom near 10B; top near 41C, about 6 to 9 mm. Anthers: Near 11C, about 3 to 4 mm.
*Pollen.*—Near 199C.
*Styles.*—Uneven length between; about 1 to 1.5 cm; thin.
*Stigmas.*—Near 13C.
*Hips.*—Hips and seeds have not been observed because the plant has never been grown to the stage of seed development and because the variety is grown for producing floral stems.

PLANT

Form: Upright; long stems, average height about 150 cm, average spread about 50 to 70 cm.
Growth: Vigorous.
Foliage: Compound 3, 5 and 7 leaflet leaves.
*Size.*—Leaflets; length about 10 cm; width about 6 cm.
*Quantity.*—Approximately 14 leaves per stem.
*Color.*—New foliage Upper Side: Near 181A. Underside: Near 180C. Mature foliage: Upper Side: Near 139A. Underside: Near 147B.
*Shape.*—Elliptic, base rounded apex acuminate.
*Texture.*—Upper Side: Glossy. Underside: Matte.
*Edge.*—Serrated.
*Serration.*—Serrate.
Petiole: Length about 2 mm.
*Top surface.*—Near 185B.
*Underside.*—Near 166B.
Stipules: About 1.5 cm; near 137B.
Auricle: Not present.
Rachis: Surface top is flat; underside is rounded with prickles.
Wood:
*New shoots.*—Color Bark: Near 145B. Wood: Near 146C.
*Old wood.*—Color Bark: Near 147B. Wood: Near 149D.
*Flower stem.*—Approximately 80 to 90 cm.
Thorns: On lower portion of stem about 3 to 4 thorns between internodes; on upper portion no prickles.
*Quantity.*—Many.
*Form.*—Small, deep concave.
*Length.*—Short length about 0.7 cm; basis width about 0.4 cm.
*Color.*—Young: About 175B. Old: About 175A.
*Position.*—Irregular.

I claim:

1. A new and distinct Hybrid Tea Rose plant of the variety substantially as shown and described.

* * * * *

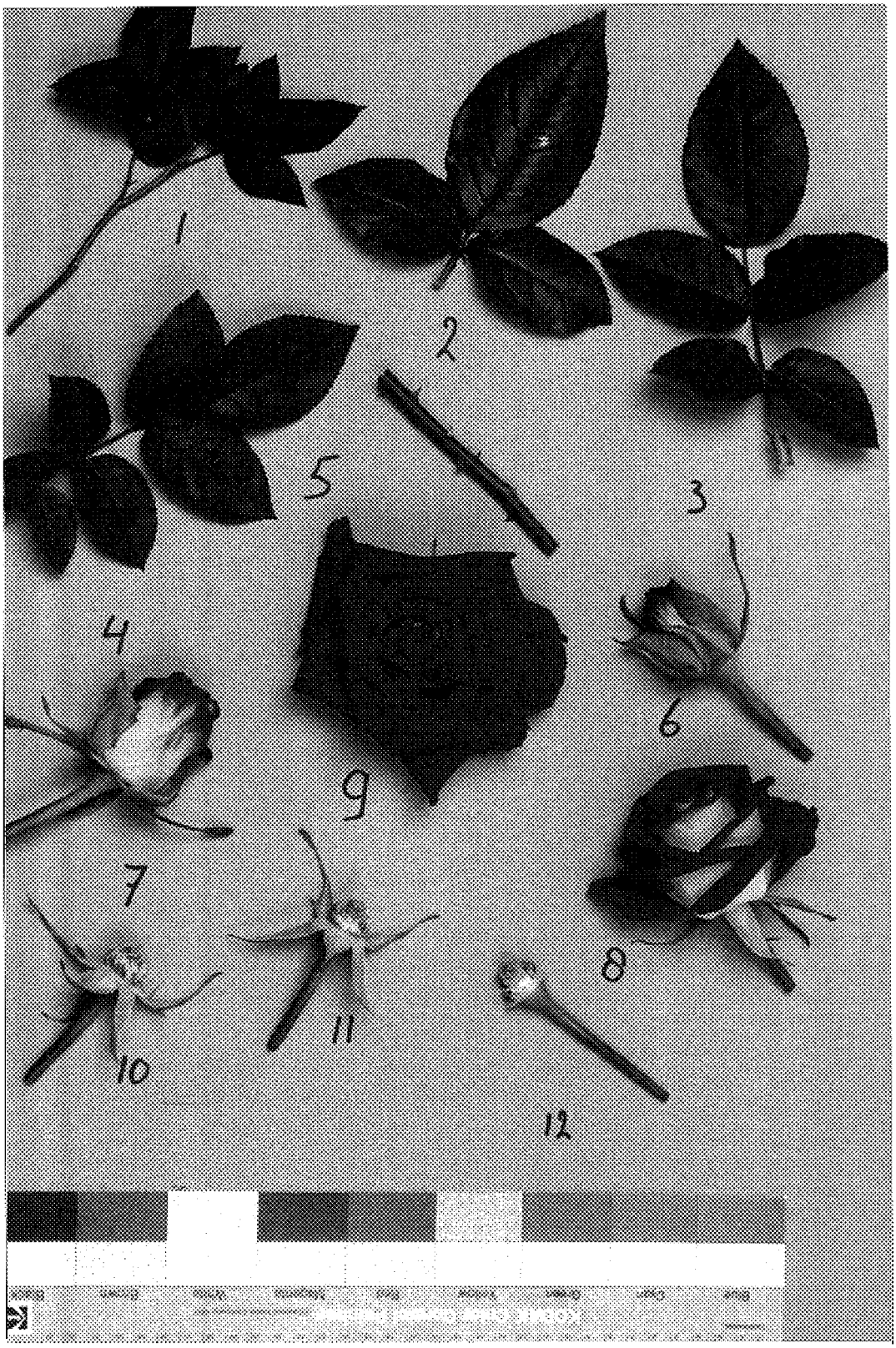
1
2
3
4
5
6
7
8
9
10
11
12